(12) United States Patent
Gray et al.

(10) Patent No.: US 6,197,588 B1
(45) Date of Patent: Mar. 6, 2001

(54) PLASTID INNER ENVELOPE MEMBRANE TARGETING POLYPEPTIDES, MANUFACTURE AND USE THEREOF

(75) Inventors: John Clinton Gray, Cambridge (GB); Jacqueline Sarah Knight, Porirua (NZ)

(73) Assignee: Advanced Technologies (Cambridge) Limited, London (GB)

( * ) Notice: Subject to any disclaimer, the term of this patent is extended or adjusted under 35 U.S.C. 154(b) by 0 days.

(21) Appl. No.: 09/029,341

(22) PCT Filed: Aug. 28, 1996

(86) PCT No.: PCT/GB96/02129

§ 371 Date: Jun. 8, 1998

§ 102(e) Date: Jun. 8, 1998

(87) PCT Pub. No.: WO97/08329

PCT Pub. Date: Mar. 6, 1997

(30) Foreign Application Priority Data

Aug. 30, 1995 (GB) .................................................. 9517674

(51) Int. Cl.$^7$ .............................. A01H 1/00; C07H 21/04; C07K 14/415; C12N 5/10; C12N 5/14

(52) U.S. Cl. .......................... 435/419; 800/278; 800/287; 800/288; 800/295; 800/298; 435/410; 435/320.1; 530/350; 536/23.1; 536/23.4; 536/23.6; 536/24.1

(58) Field of Search ..................................... 800/278, 287, 800/288, 295, 298; 435/410, 419, 320.1; 530/350; 536/23.1, 23.4, 23.6, 24.1

(56) References Cited

U.S. PATENT DOCUMENTS 5,545,817 * 8/1996 McBride et al. .
5,877,402 * 3/1999 Maliga et al. .

OTHER PUBLICATIONS

Anderson & Smith, 1986, "Synthesis of the small subunit of ribulose–bisphosphate carboxylase frome genes cloned into plasmids containing the SP6 promoter," *Biochem. J.* 240:709–715.

Cline et al., 1985, "Precursors to two nuclear–encoded chlorplast proteins bind to the outer envelope membrane before being imported into chloroplasts", *J. Biol. Chem.* 260:3691–3696.

Douwe de Boer & Weisbeek, 1991, "Chloroplast protein topogenesis: Import, sorting and assembly", *Biochimica et Biophysica Acta* 1071:221–253.

Dreses–Werringloer et al., 1991, "cDNA sequence and deduced amino acid sequence of the precursor of the 37–kDa inner envelope membrane polypeptide from spinach chloroplasts", *Eur. J. Biochem.* 195:361–368.

Fischer et al., 1994, "The 24 kDa outer envelope membrane protein from spinach chloroplasts: Molecular cloning, in vivo expression and import pathway of a protein with unusual properties", *Plant Mol. Biol.* 25:167–177.

Fliege et al., 1978, "Specific transport of inorganic phosphate, 3–phosphoglycerate and triosephosphates across the inner membrane of the envelope in spinach chloroplasts", *Biochimica et Biophysica Acta* 50:232–247.

Flogge & Heldt, 1979, "Phosphate translocator in chloroplasts: Identification of the functional protein and characterization of its binding site", pp. 373–382, (E. Quagliariello et al., eds.) Elsevier/North–Holland Biomedical Press, Göttingen.

Flügge et al., 1989, "The triose phosphate–3–phosphoglycerate—phosphate translocator from spinach chloroplasts: Nucleotide sequence of a full–length cDNA clone and import of the in vitro synthesized precursor protein into chloroplasts", *EMBO Journal* 8:39–46.

Friedrich & Kadner, 1987, "Nucleotide sequence of the uhp region of *Escherichia coli*", *J. Bacteriol.* 169:3556–3563.

Gearing & Nagley, 1986, "Yeast mitochondrial ATPase subunit 8, normally a mitochondrial gene product, expressed in vitro and imported back into the organelle", *EMBO J.* 5:3651–3655.

Hirsch et al., 1994, "A receptor component of the chloroplast protein translocation machinery", *Science* 266:1989–1992.

Joyard et al., 1982, "Characterization of envelope membrane polypeptides from spinach chloroplasts", *J. Biol. Chem.* 257:1095–1101.

Keegstra et al., 1989, "Chloroplastic precursors and their transport across the envelope membranes", *Annu. Rev. Plant Physiol. Plant Mol. Biol.* 40:471–501.

Knight & Gray, 1994, "Expression of genes encoding the tobacco chloroplast phosphate translocator is not light–regulated and is repressed by sucrose", *Mol. Gen. Genet.* 242:586–594.

Ko et al., 1992, "Isolation and characterization of a cDNA clone encoding a cognate 70–kDa heat shock protein of the chloroplast envelope", *J. Biol. Chem.* 267:2986–2993.

Li et al., 1991, "Targeting of proteins to the outer envelope membrane uses a different pathway than transport into chloroplasts", *The Plant Cell* 3:709–717.

(List continued on next page.)

Primary Examiner—Phuong T. Bui
(74) Attorney, Agent, or Firm—Pennie & Edmonds LLP

(57) ABSTRACT

A polypeptide amino acid sequence capable of targeting the plastid inner envelope membrane of a plant, and a nucleotide sequence therefor, are described, as well as a chimaeric gene comprising a gene promoter, a nucleotide sequence encoding a polypeptide capable of targeting the plastid inner envelope membrane of a plant, or a variant, derivative or homologue thereof, a coding sequence and a terminator sequence. A method of transforming plants, such as potato and tobacco, using the targeting sequence so as to increase starch production is also described. The targeting sequence can be used in many other applications.

24 Claims, 6 Drawing Sheets

OTHER PUBLICATIONS

Figure 1A:
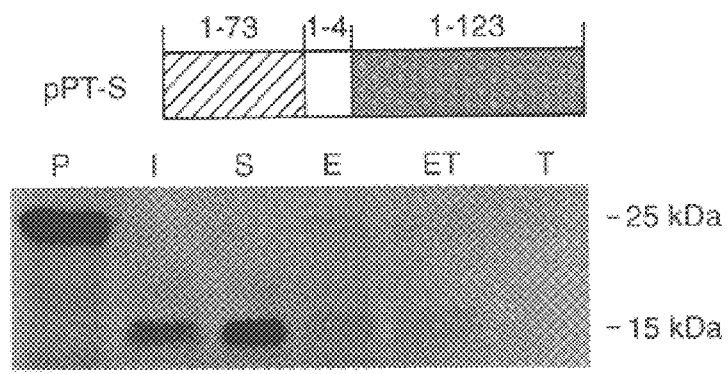

Li et al., 1992, "Information for targeting to the chloroplastic inner envelope membrane is contained in the mature region of the maize Bt1–encoded protein", *J. Biol. Chem.* 267:18999–19004.

Li & Shore, 1992, "Reversal of the orientation of an integral protein of the mitochondrial outer membrane", *Science* 256:1815–1817.

Oblong & Lamppa, 1992, "Identification of two structurally related proteins involved in proteolytic processing of pre–cursors targeted to the chloroplast", *EMBO J.* 11:4401–4409.

Ostrem et al., 1989, "Deletion of the carboxyl–terminal portion of the transit peptide affects processing but not import or assembly of the small subunit of ribulose–1, 5–bisphosphate carboxylase", *J. Biol. Chem.* 264:3662–3665.

Perry & Keegstra, 1994, "Envelope membrane proteins that interact with chloroplastic precursor proteins", *Plant Cell* 6:93–105.

Salomon et al., 1990, "Sequence analysis and protein import studies of an outer chloroplast envelope polypeptide", *Proc. Natl. Acad. Sci. USA* 87:5778–5782.

Schnell et al., 1994, "Isolation of components of the chloroplast protein import machinery", *Science* 266:1007–1012.

Schulz et al., 1993, "Expression of the triose phosphate translocator gene from potato is light dependent and restricted to green tissues", *Mol. Gen. Genet.* 238:357–361.

Steck & Yu, 1973, "Selective solubilization of proteins from red blood cell membranes by protein perturbants", *J. Supramol. Structure* 1:220–232.

Sullivan et al., 1991, "Analysis of maize Brittle–1 alleles and a defective suppressor–mutator–induced mutable allele", *Plant Cell* 3:1337–1348.

Waegmann & Soll, 1991, "Chacterization of the protein import apparatus in isolated outer envelopes of chlorplasts", *The Plant J.* 1:149–158.

Willey et al., 1991, "Molecular cloning and structural analysis of the phosphate translocator from pea chloroplasts and its comparison to the spinach phosphate translocator", *Planta* 183:451–461.

Wu et al., 1994, "Identification of chloroplast envelope proteins in close physical proximity to a partially translocated chimeric precursor protein", *J. Biol. Chem.* 269:32264–32271.

* cited by examiner

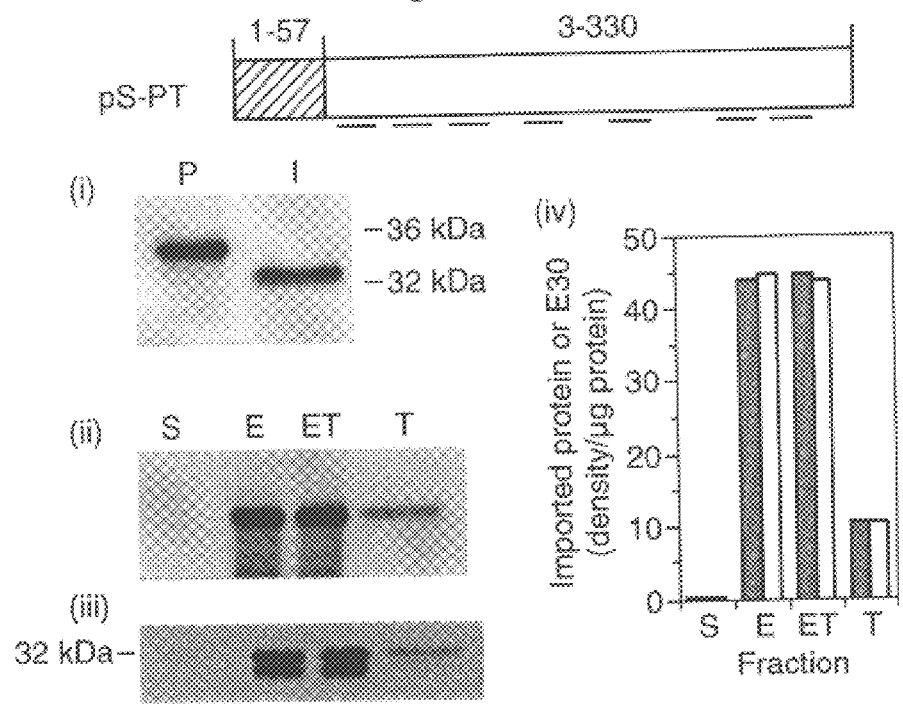
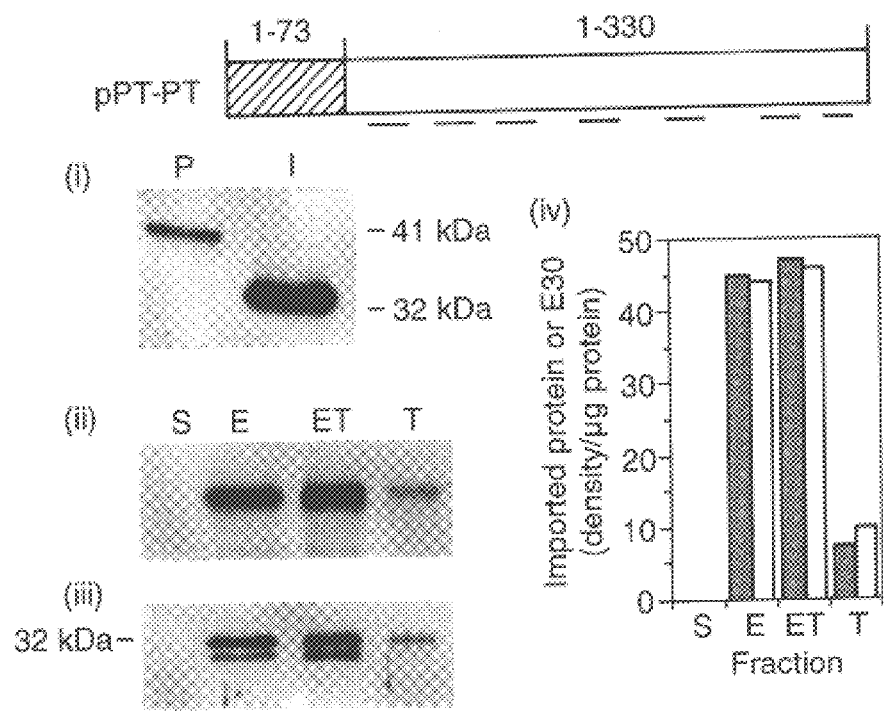

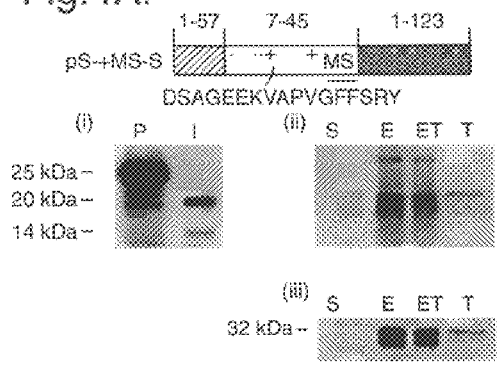
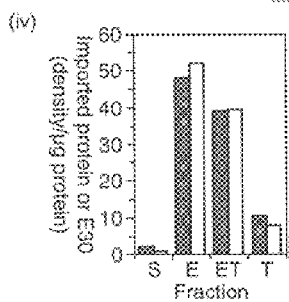
Fig. 4A.
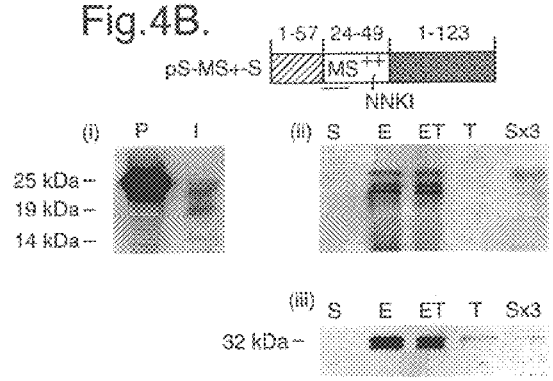
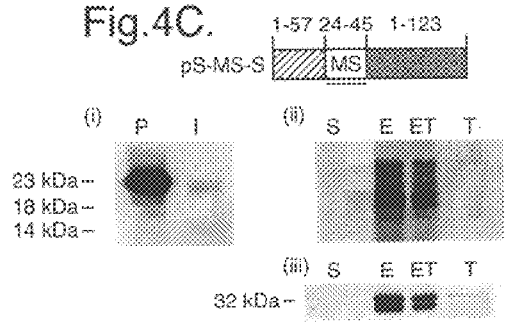
Fig. 4B.
Fig. 4C.

pPT-PT

C   W pS-PT

C   W pS-PTMS1-S

C   W pS-+MS-S

C   W pS-MS+-S

C   W pS-MS-S

C   W pPT-PT pS-+MS-S pS-PT pS-MS+-S pS-PTMS1-S pS-MS-S

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 22 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Pro Ala Leu Thr Thr Gly Phe Phe Phe Thr Trp Tyr Phe Leu Asn
1             5                   10                15

Val Ile Phe Asn Ile Leu
          20

(2) INFORMATION FOR SEQ ID NO:2:

(i) SEQUENCE CHARACTERISTICS:
      (A) LENGTH: 66 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:2:

CCAGCTCTTA CTACCGGTTT TTTCTTCTTC ACTTGGTACT TCTTGAATGT GATTTTCAAC    60

ATCCTC    66

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:3:

CGCGGCATGC AGATCTTCTT GTTGAGGAT    29

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:4:

CGCGGCATGC TCAGCAACTT CAGCAGGTT    29

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:5:

GCGCGCATGC CCGATTCCGC TGGTGAAG    28

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:6:

GCCGCTGCAG CGAGGATGTT GAAAATCAC    29

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

GCGCGCATGC CAGCTCTTAC TACC                                            24

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

CGCGGCATGC AGATCTTCTT GTTGAGGAT                                       29

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

GCGGGCATGC CAGCTCTTAC TACC                                            24

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:10:

GCCGCTGCAG GCGAGGATGT TGAAAATCAC                                      30

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:11:

CGCGCGCATG CTGGCTTTCT TAAACCAGG                                       29

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:12:

CGGGATCCGA ATTCTTATGC CACTGTCAAC TGCTH                                35

PLASTID INNER ENVELOPE MEMBRANE TARGETING POLYPEPTIDES, MANUFACTURE AND USE THEREOF

The present invention relates to plastid inner envelope membrane targeting polypeptides; manufacture and use thereof.

Plastids are organelles present in all plants except blue-green algae, bacteria and fungi. They have various functions and forms but all are bounded by a double membrane envelope. Plastids, including amyloplasts, chromoplasts, leucoplasts and chloroplasts are derived from proplastids in the meristematic cells of plants. The proplastids develop into the various plastid types depending on the cell type and its location in the plant. Amyloplasts, are starch-storage plastids in seeds, tubers and other storage tissues; chromoplasts are brightly coloured carotenoid-containing plastids found in fruits, such as tomatoes and oranges, and in flowers; leucoplasts are colourless plastids found in all other plant cells and often modified for the storage of food; chloroplasts contain the photosynthesis pigments and carry out photosynthesis.

Chloroplasts are complex organelles consisting of six compartments including the outer and inner envelope membranes, the intermembrane space, the stroma, the thylakoid membrane and the thylakoid lumen. Consequently, information is required not only for the targeting of nuclear-encoded proteins to the chloroplast but for sorting to the correct intra-organellar location. The majority of nuclear-encoded chloroplast proteins are synthesised as higher molecular weight precursors with an N-terminal presequence (Keegstra et al., 1989). The presequence directs the protein to the chloroplast surface where it interacts with a proteinaceous receptor in an energy-dependent manner (Cline et al., 1985) and is subsequently translocated across the double envelope membrane. Two approaches, crosslinking of precursors to the import apparatus (Perry and Keegstra, 1994; Wu et al., 1994) and the isolation of translocation complexes (Waegemann and Soll, 1991; Schnell et al., 1994) have enabled the identification of several of the components of the chloroplast import machinery. Maturation of imported protein occurs in the stroma and is catalysed of the stromal processing peptidase (SPP; Oblong and Lamppa, 1992).

Targeting of proteins to the thylakoid membrane and to the thylakoid lumen have been well studied (see de Boer and Weisbeek, 1991) but there have been few studies of envelope membrane targeting.

Most studies have involved the outer envelope membrane and it is not clear what part of the proteins provides the targeting information (Salomon et al., 1990; Li et al., 1990; Ko et al., 1992; Fischer et al., 1994). However, a recently identified outer envelope component of the import machinery does have an N-terminal presequence (Hirsch et al., 1994).

The targeting of three inner envelope membrane proteins has also been studied. These include a 37 kD protein of unknown function (Dreses-Werringloer et al., 1991), the maize Bt1 protein identified as a putative amyloplast membrane metabolite translocator (Sullivan et al., 1991) and the phosphate translocator. The phosphate translocator (PT) is the most abundant chloroplast inner envelope membrane protein (Flügge and Heldt, 1979) and catalyses the export of photosynthate across the inner envelope membrane (Fliege et al., 1978). The mature PT protein is approximately 36 kD and is very hydrophobic containing seven putative membrane-spanning regions. All three inner envelope proteins are synthesised with N-terminal presequences and their import by chloroplasts is both energy-dependent and receptor-mediated (Flügge et al., 1989; Dreses-Werringloer et al., 1991; Li et al., 1992).

The PT precursor proteins from spinach, pea, potato and tobacco have presequences of 72–84 amino acid residues (Flügge et al., 1989; Willey et al., 1991; Schulz et al., 1993; Knight and Gray, 1994) whereas the presequence of the 37 kD precursor protein is 21 amino acid residues (Dreses-Werringloer et al., 1991). The presequences of both proteins are reported to contain features, such as a higher hydroxyl amino acid and a lower arginine content as well as the potential to form an amphiphilic α-helix, which distinguish them from other stromal or thylakoid-targeted proteins. It was suggested that these unusual presequences may be responsible for inner envelope membrane targeting as well as chloroplast targeting (Willey et al., 1991; Dreses-Werringloer et al., 1991).

The present invention has resulted from the identification of residues required for envelope targeting of the phosphate translocator. A number of chimaeric proteins comprising portions of the inner envelope membrane PT fused to the stromal small subunit of ribulose-1,5-bisphosphate carboxylase (SSU Rubisco) were produced and the location of these proteins after their import by isolated chloroplasts was determined. The results indicate that the PT presequence contains only stromal-targeting information and that the mature PT protein is responsible for inner envelope membrane targeting. Further refinement of the chimaeric proteins shows that the N-terminal hydrophobic region of the mature PT protein can direct a stromal protein to the inner envelope membrane demonstrating that targeting information is contained within this region.

The work described herein demonstrates that amino acid residues 24–45 (SEQ ID NO: 1) of the phosphate translocator provide information sufficient for direction of a protein to the inner envelope membrane.

Sequences able to target the chloroplast inner envelope should also target to the envelope of other plastid types in respective cells.

It is an object of the present invention to target the plastid inner envelope membrane of a plant cell.

It is a further object to use this technology to improve the synthesis and storage of starch in plants. Other metabolic processes plastids may also be altered.

Thus according to the method below there is provided a nucleotide sequence encoding a polypeptide comprising amino acid sequence PALTTGFFFFTWYFLNVIFNIL (SEQ ID NO: 1), or an amino acid sequence variant thereof or a derivative thereof. The amino acid sequence SEQ ID NO: 1 is from the pea phosphate translocator. Homologous from other species, and variants and derivatives thereof, are also employed by the present invention. The polypeptide is able to target a plastid inner envelope membrane of a plant cell. Preferably the amino acid sequence is a purified sequence.

The polypeptide sequence may comprise one or more heterologous amino acids joined to the amino acid sequence shown or a variant or derivative thereof. It may retain one or more amino acids from the molecule from which it is derived; for example the polypeptide may comprise one or more amino acids which flank the amino acid sequence SEQ ID NO: 1 in the pea phosphate translocator, or a homologue from another species.

Amino acids joined to the membrane targeting sequence may form a protein domain. Preferably, the sequence of amino acids forms a functional domain. The amino acids may comprise a sequence derived from a membrane transporter or translocator protein, an enzyme, e.g. an enzyme involved in biosynthesis or catabolism, a protein or polypeptide involved in DNA replication or signal transduction including a sequence involved in the control of the growth of cells and hence the development of plant form and function.

The plastid inner envelope is the main permeability barrier of the plastids and therefore targeting transporter or translocator proteins to the envelope may be carried out to change the permeability of the membrane. This may be used to allow the uptake into plastids of compounds that would not normally be transported or to increase uptake or efflux of compounds that are normally transported but at rather slow rates. The transporter proteins (or their genes) may be from any source (animal, plant, fungal, bacterial). One specific example is to increase the permeability of potato tuber amyloplast membranes to glucose 6-phosphate by fusing a gene encoding a glucose 6-phosphate phosphate transporter, e.g. that encoded by the uhpT gene from *Escherichia coli* (Friedrich and Kadner, 1987) to the targeting sequence, with the aim of altering starch production.

Transporter proteins transporting an enormous range of molecules, including sugars, amino acids, metal ions, etc. have been described and their genes isolated in many instances. The introduction of any of these transporters into plastid envelopes may be the starting point for changing the metabolic processes in plastids. It may be possible to get plastids to produce plastics and other polymers if the monomers can be transported across the envelope into the plastid. An advantage of using the chloroplast is that it is the primary source of energy for the plant and the energy may be used directly for synthetic purposes.

The plastid envelope is also the site of various enzymes involved in the synthesis of lipids, carotenoids and tetrapyrroles. New membrane-bound enzymes may be targeted to the envelope to change the biosynthetic capability. The envelope is also involved in DNA replication in plastids. This process may be manipulatable by introducing proteins from bacteria or other organisms. It is also thought that the plastid envelope is used in signal transduction pathways relaying information to other parts of the cell. This may be important for controlling the growth of cells and hence the development of plant form and function.

The targeting sequence described and claimed herein may be used to enable changes in the protein constituents of the envelope membrane and intervention in the processes going on in the envelope and inside plastids. Because chloroplasts are the major source of useful energy in the plant, targeting the chloroplast envelope is the key to changing many processes in plants.

Amyloplasts and other plastids may also be targeted.

In principle, any amino acid sequence including a peptide or polypeptide, independently folding protein domain or protein domains may be joined to the targeting sequence. This may be at the C-terminal or the N-terminal end of the polypeptide or at both ends, involving identical, similar or different protein sequences. "Joining" generally involves use of recombinant nucleic acid technology to generate a fusion polypeptide by expression from encoding nucleic acid therefor.

An amino acid sequence variant may comprise one or more changes, e.g. by way of addition, substitution, insertion or deletion of one or more amino acids, compared with wild type. Any such change should generally not abolish the ability of the polypeptide to perform its function, though it may increase or decrease this ability depending on the nature of the change. A derivative has some modification compared with the naturally-occurring polypeptide, which may be chemical. This may include the chemical or enzymatical attachment of carbohydrate structures, nucleic acids or other chemical compounds.

Changes may be made to the amino acid sequence, compared with wild-type, by providing and manipulating suitable encoding nucleic acid used for the production of the polypeptide in an expression system.

The present invention further provides nucleic acid comprising a sequence of nucleotides encoding a polypeptide able to target a plastid inner envelope membrane as provided herein.

The encoding sequence of nucleotides advantageously comprises the sequence SEQ ID NO: 2, or a variant, homologue or derivative thereof. A sequence variation, addition, insertion, substitution and/or deletion of one or more nucleotides may or may not be reflected in an alteration in the encoded amino acid sequence, dependent on the degeneracy of the genetic code.

The nucleic acid may comprise an appropriate regulatory sequence operably linked to the encoding sequence for expression of the polypeptide. Expression from the encoding sequence may be said to be under the control of the regulatory sequence.

Also provided by the present invention are a vector comprising nucleic acid capable of targeting a plastid inner envelope membrane particularly and expression vector from which the encoded polypeptide can be expressed under appropriate conditions, and a host cell containing any such vector or nucleic acid. Preferably the vector is suitable for transformation into a plant cell. Preferably the host cell is a plant cell.

A convenient way of producing a polypeptide according to the present invention is to express nucleic acid encoding it. Accordingly, the present invention also encompasses a method of making a polypeptide according to the present invention, the method comprising expression from nucleic acid encoding the polypeptide, either in vitro or in vito. The nucleic acid may be part of an expression vector. Expression may conveniently be achieved by growing a host cell, containing appropriate nucleic acid, under conditions which cause or allow expression of the polypeptide. Systems for cloning and expression of a polypeptide in a variety of different host cells are well known to the man skilled in the art and will not be repeated here.

A vector comprising nucleic acid according to the present invention need not include a promoter, particularly if the vector is to be used to introduce the nucleic acid into cells for recombination into the genome.

Thus, a further aspect of the present invention provides a host cell containing nucleic acid as disclosed herein. A still further aspect provides a method comprising introducing such nucleic acid into a host cell. The introduction may employ any available technique known to the skilled man.

DNA can be transformed into plant cells using any suitable technology, such as a disarmed Ti-plasmid vector carried by Agrobacterium exploiting its natural gene transfer ability (EP-A-0270355, EP-A-0116718, Bevan, M. W., Nucleic Acid Res., 12, 8711–8721, 1984), particle or microprojectile bombardment (U.S. Pat. No. 5,100,792), EP-A-0444882, EP-A-0434616) microinjection (WO 92/09696, WO 94/00583, EP 0331083, EP 0175966), electroporation (EP 0290395, WO 87/06614) or other forms of direct DNA uptake (DE 4005152, WO 90/12096, U.S. Pat. No. 4,684, 611).

In one preferred embodiment the nucleic acid of the invention is integrated into the genome of a host cell and a plant regenerated therefrom.

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention.

The present invention provides a chimaeric gene comprising a gene promoter, a nucleotide sequence encoding a polypeptide capable of targeting the plasmid inner envelope membrane of a plant, or a variant, derivative or homologue thereof, a coding sequence comprising a reporter sequence or any other sequence which confers an identifiable character to a transformed plant, and a terminator sequence.

The nucleotide sequence may also be known herein as the targeting sequence.

Advantageously the nucleotide sequence comprises the sequence SEQ ID NO. 2, or a variant, homologue or derivative thereof.

As used herein a chimaeric gene is a recombinant DNA molecule which comprises sequences from more than one organism.

The present invention further provides a method of targeting a protein or polypeptide for a particular plant characteristic into the plastid inner envelope membrane of a plant, comprising introducing a chimaeric gene comprising a suitable promoter, a nucleotide sequence encoding a polypeptide capable of targeting the plastid inner envelope membrane, or a variant, derivative or homologue thereof, a coding sequence for said protein or polypeptide for said plant characteristic and a terminator into a plant.

Preferably the coding sequence of the chimaeric gene is a transporter sequence required to change a particular plant characteristic, in order to alter or change a particular plant characteristic.

Advantageously, the transporter sequence is the coding sequence for the hexose phosphate translocator. Targeting of the hexose phosphate translocator to the plastid inner envelope membrane should result in an increase in starch production in the transformed plant. ADP glucose can also be translocated.

Other suitable transporter sequences could be sequences for translocators for intermediates in any of the following: starch, synthesis, pigment biosynthesis, oil biosynthesis and lipid biosynthesis.

The present invention also provides a transformed plant transformed according to the method of the invention. The transformed plant may be a dicotyledonous species, such as potato, tobacco, cotton, lettuce, melon, squash, cucumber, pea, rape, soyabean, sugar beet or sunflower, or a monocotyledonous species, such as wheat, barley, rye, rice or maize.

Plants which comprise a plant cell according to the invention are also provided, along with any part or propagule thereof, seed, selfed or hybrid progeny and descendants and clones, and any part or propagule thereof.

All documents mentioned in the text are incorporated herein by reference.

Figure 1B:
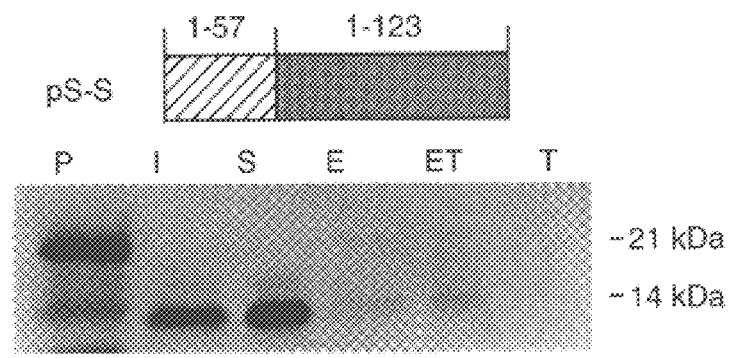
Figure 1C:
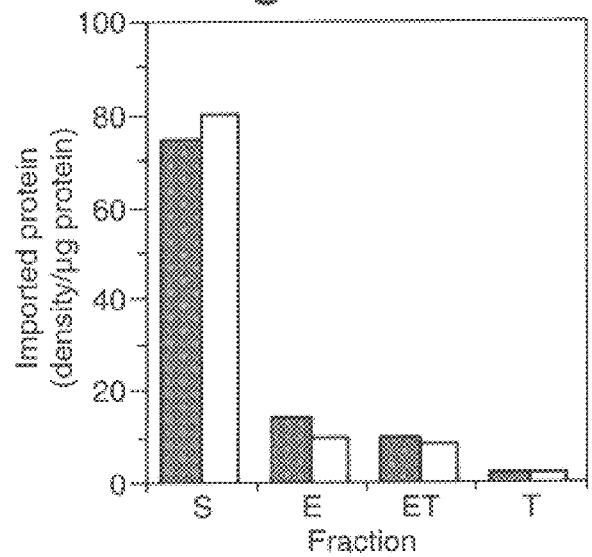

In order that the invention can be easily understood and readily carried into effect reference will now be made, by way of example, to the accompanying FIGURES, in which;

FIGS. 1A–1C The PT Presequence Contains Stromal Targeting Information.

Panel 1A, pPT-S; panel 1B, pS-S. Diagrammatic representations of precursor proteins are shown (top). Light hatched box, SSU mature protein; open box, PT mature protein, closed box, SSU mature protein; dark hatched box, SSU presequence. Proteins (10 µg) from each fraction was electrophoresed on SDS-15% polyacrylamide gels, fixed in boiling 5% (w/v) trichloroacetic acid for 5 min, incubated in Amplify ) Amersham International) for 15 min, dried and exposed to Hyperfilm-βmax (Amersham International). (1C) Imported protein in sub-chlorplast fractions was quantified by scanning the fluorographs with a Molecular Dynamics 300A laser scanning densitomer. In the bar chart showing the quantification of the imported protein the following applies: closed bar, imported pPT-S; open bar, imported pS-S; P, precursor protein; I, imported products; S, stromal fraction; E, envelope fraction; ET, mixed envelope-thylakoid fraction; T, thylakoid fraction. This type of description of the bar charts in the accompanying Figures is followed below.

FIGS. 2A–2B Envelope-targeting Information Resides in the Mature PT Protein.

Panel 2A, pPT-S; Panel 2B, pPT-PT. Diagrammatic representation of the precursor proteins are shown (top). Dark hatched box, SSU presequence; open box, PT mature protein; light hatched box, PT presequence; dashes, putative membrane-spanning regions. (i) Precursor proteins were imported by pea chloroplasts to produce imported products. (ii) Sub-chloroplast fractions were isolated as described in FIGS. 1A–1C proteins (10 µg) from each fraction were electrophoresed on SDS-15% polyacrylamide gels and the imported protein visualised by autoradiography. (iii) Endogenous PT protein in sub-chloroplast fractions were visualised by immunoblotting with antibodies against the spinach E30 protein. (iv) Imported protein and endogenous PT protein is sub-chloroplast fractions were quantified by scanning (ii and iii) as described in FIGS. 1A–1C. In the bar charts: closed bars, imported protein; open bars, endogenous PT; P, precursor protein; I, import products; S, stromal fraction; E, envelope fraction; ET, mixed envelope-thylakoid fraction; T, thylakoid fraction.

FIGS. 3A–3D The N-terminal Regional of the Mature PT Protein Contains Envelope-targeting Information.

Panel 3A, pPTMS1-S, panel 3B, pPTMS1+2-S; panel 3C, pS-PTMS1-S; panel 3D, pS-PTMS1+S-S. Diagrammatic representations of the precursor proteins are shown (top). Light hatched box, PT presequence; open box, PT mature protein, closed box, SSU mature protein; dark hatched box, SSU presequence; dashes, putative membrane-spanning regions. (i), (ii), (iii) and (iv) are identical to those described in FIGS. 2A–2B. In the bar charts: closed bars, imported protein; open bars, endogenous PT; P, precursor protein; I, import products; S, stromal fraction; E, envelope fraction; ET, mixed envelope-thylakoid fraction; T, thylakoid fraction.

FIGS. 4A–4C The N-terminal Hydrophobic Region of the Mature PT Protein contains Envelope-targeting Information.

Panel 4A, ps-+MS-S; panel 4B, pS-MS+-S; panel 4C, pS-MS-S. Diagrammatic representations of precursor proteins are shown (top). Dark hatched box, SSU presequence; closed box, SSU mature protein; open box, PT mature protein; dash, putative membrane span (MS); letters, amino acid sequence; + and −, charges of amino acid residues. (i), (ii), (iii) and (iv) are identical to those described in FIGS. 2A–2B except electrophoresis of 30 µg stromal protein is shown in 4B(ii) and 4B(iii). In the bar chart: closed bars, imported protein; open bars, endogenous PT; P, precursor protein; I, import products; S, stromal fraction; E, envelope fraction; ET, mixed envelope-thylakoid fraction; T, thylakoid fraction; S×3, 3-fold loading of stromal fraction.

FIGS. 5A–5F Extractability of Envelope-associated Chimaeric Proteins with 0.1M Sodium Hydroxide.

Panel 5A, pPT-PT; panel 5B, pS-PT; panel 5C, pS-PTMS1-S; panel 5D, pS-+MS-S; panel 5E, pS-MS+-S; panel 5F, pS-MS-S. Precursor proteins were imported by pea chloroplasts and a total envelope fraction isolated as described in FIGS. 1A–1C. An equal volume of envelopes (C) and 0.1M NaOH washed envelopes (W) were electrophoresed on SDS-15% polyacrylamide gels and imported proteins visualised by autoradiography.

FIGS. 6A–6F. The N-terminal Hydrophobic Region of the Mature PT Protein Directs the SSU Rubisco to the Inner Envelope Membrane.

Panel 6A, pPT-PT, panel 6B, pS-PT; panel 6C, pS-PTMS1-S; panel 6D, pS-+MS-S; panel 6E, ps-MS+-S; panel 6F, pS-MS-S. Precursor proteins were imported, chloroplasts lysed hypertonically and sub-chloroplast fractions isolated by sucrose density gradient centrifugation as described in Methods. Protein (10 µg) from each fraction was electrophoresed on SDS-15% polyacrylamide gels, imported protein visualised by autoradiograph (i) and endogenous PT protein by immune detection (ii) as described in FIGS. 2A–2B. In the bar chart: I, import products; S, stromal fraction; OE, outer envelope fraction; IE, inner envelope fraction; T, thylakoid fraction.

METHODS

Materials

Radiochemicals were purchased from Amersham International (Amersham, UK) and enzymes for recombinant DNA techniques were obtained from either Amersham International or Boehringer Mannheim U.K. (Lewes, U.K.). Oligonucleotides were synthesised at the Cambridge Centre for Molecular Recognition facility. Pea (Pisum sactivum var. Feltham First) seeds were germinated and grown as described by Knight and Gray (1994).

Construct Production

The plasmid pPPT8 is a derivative of pSP64 (Promega, Madison, Wis., USA) with the pea PT cDNA cloned into the EcoRI restriction site in the sense orientation with respect to the SP6 promoter (Willey et al., 1991). To produce the construct pSPT-S a 260 bp EcoRI-PstI restriction fragment of pPPT8 encoding the 73 amino acid residue PT presequence and 4 amino acid residues of the PT mature protein was cloned into EcoRI-PstI-digested pUBR. The latter (pUBR) was produced by cloning a 690 bp BamHI-PstI restriction fragment of pSMS58 (Anderson and Smith, 1986) encoding the SSU Rubisco mature protein into similarly digested pUBS (multiple cloning site of Bluescript KS+ in pUC18). To produce the construct pPT-S a 260 pb HindIII-PstI restriction fragment encoding the PT presequence and the first 2 amino acid residues of the PT mature protein was excised from pPPT8 and replaced with a 210 bp HindIII-PstI restriction fragment from PSPTP19 (Anderson and Smith, 1986) encoding the 57 amino acid residue SSU Rubisco presequence.

To produce the construct pPTMS1-S the polymerase chain reaction (PCR) was used to introduce an inframe SphI restriction site 401 bp from the 5' end of the pea PT cDNA. The sense primer was equivalent to the SP6 sequencing primer (Boehringer Mannheim) and the antisense primer was the oligonucleotide 5'-CGC GGC ATG CAG ATC TTC TTG TTG AGG AT-3' (SEQ ID NO: 3). The underlined portion of the primer represents the restriction site used for cloning. The reaction contained 10 ng of template DNA (pPPT8), 1 µM each primer, 200 µM each of dATP, TTP, dCTP, dGTP (Pharmacia Biosystems Ltd., Milton Keynes, U.K.), 1× Taq polymerase buffer and 2 units of AmpliTaq Taq polymerase (Perkin-Elmer Cetus, Beaconsfield, U.K.). The reaction was at 95° C. for 2 min, 32° C. for 1 min and 72° C. for 3 min for 2 rounds followed by 10 rounds at 95° C. for 2 min, 42° C. for 1 min and 72° C. for 3 min. The 500 bp product encoding the PT presequence and the first 49 amino acid residues of the PT mature protein was digested with SphI and EcoRI and cloned into SphI-EcoRI-digested pUBR. A 1.1. kpb BamHI-EcoRI restriction fragment from this construct, encoding pPTMS1-S, was then cloned into BamHI-EcoRI-digested pSP65 (Promega). The construct pPTMS1+2-S was produced using PCR to introduce an inframe SphI restriction site 533 bp from the 5' end of the pea PT cDNA. The same PCR conditions were used as those for the production of pPTMS1-S except the antisense primer was the oligonucleotide 5'-CGC GGC ATG CTC AGC AAC TTC AGC AGG TT-3' (SEQ ID. NO. 4). The underlined portion of the primer represents the restriction site used for cloning. The 632 bp product encoding the PT presequence and the first 93 amino acid residues of the mature PT protein was digested with SphI and EcoRI and cloned into SphI-EcoRI-digested pUBR. A 1.2 kbp BamHI-EcoRI restriction fragment, encoding pPTMS1+2-S, from this construct was cloned into BamHI-EcoRI-digested pSP65.

To produce the construct pS-PTMS1-S, a 830 bp PSTI-BamHI restriction fragment from the construct pPTMS1-S encoding amino acid residues 3 to 49 of the PT mature protein attached inframe to the 123 amino acid residue SSU Rubisco mature protein was cloned into PstI-BamHI-digested pSPTP19. The construct pS-PTMS1+2-S was produced by digesting the construct pPTMS1+2-S with PstI and BamHI to release a 958 bp restriction fragment, encoding amino acid residues 3 to 93 for the mature PT protein attached inframe to the SSU Rubisco mature protein, which was cloned into PstI-BamHI-digested pSPTP19.

To produce the construct pS-+MS-S, PCR was used to introduce an inframe-SphI restriction site 271 bp and an inframe PstI restriction site 388 bp from the 5' end of the pea PT cDNA. The sense primer was the oligonucleotide 5'-GCG CGC ATG CCC GAT TCC GCT GGT GAS G-3' (SEQ ID NO: 5) and the antisense primer was the oligonucleotide 5'-GCC GCT GCA GCG AGG ATG TTG AAA ATC AC-3' (SEQ ID NO: 6). The underlined portions of the primers represent the restriction sties used for cloning. The reaction contained 10 ng template DNA (pPPT8), 1 µM each primer, 200 µM each of dATP, TTP, dGTP, dCTP, 1× pfu polymerase buffer (Stratagene, La Jolla, Calif.) and 0.025 units/µl cloned pfu DNA polymerase (Stratagne). The reaction was at 95° C. for 1 min, 30° C. for 1 min and 72° C. for 5 min followed by 17 rounds at 95° C. for 1 min, 60 ° C for 1 min and 72° C. for 5 min. The 137 bp product encoding amino acid residues 7 to 45 of the mature PT protein was digested with SphI and PstI and cloned into SphI-PstI-digested pSPTP19 to produce ps-+MS.

To produce the construct pS-MS+-S, PCR was used to introduce inframe SphI sites 323 bp and 401 bp from the 5' end of the pea PT cDNA. The sense primer was oligonucleotide 5'-GCG CGC ATC CCA GCT CTT ACT ACC-3' (SEQ ID NO: 7) and the antisense primer was the oligonucleotide 5'-CGC GGC ATG CAG ATC TTC TTG TTG AGG AT-3' (SEQ ID NO: 8). The underlined portion of the primers represents the restriction site used for cloning. The reaction conditions were identical to those used for the production of pS-+MS-S. The 98 bp PCR product encoding amino acid residues 24 to 49 of the mature PT protein was digested with SphI and cloned into SphI-digested pSS19 to produce pS-MS+-S. pSS19 has a unique SphI restriction site between the regions encoding the SSU Rubisco presequence and mature protein and was made by cloning a 690 bp SphI-BamHI fragment of pS-PTMS1-S into SphI-BamHI-digested pPTP19.

To produce the construct pS-MS-S, PCR was used to introduce an inframe SphI restriction site 323 bp and an inframe PstI site 388 bp from the 5' end of the pea PT cDNA. The sense primer was the oligonucleotide 5'-GCG GGC ATG CCA GCT CTT ACT ACC-3' SEQ ID NO: 9) and the antisense primer was the oligonucleotide 5'-GCC GCT GCA GGC GAG GAT GTT GAA AAT CAC-3' (SEQ ID NO: 10). The underlined portion of the primers represents the restriction sites used for cloning. The reaction conditions were identical to those used for the production of pS-+MS-S. The 87 bp PCr product encoding amino acid residues 24 to 45 of the mature PT protein was digested with SphI and PstI and cloned into SphI-PstI-digested pSPTP19 to produce pS-MS. A 690 bp PstI-BamHI fragment from pSMS58 encoding the SSU Rubisco mature protein was cloned into the PstI-BamHI-digested pS-Ms to produce pS-MS-S.

Transcription and Translation in Vitro

Chimaeric protein precursors were synthesised by transcription using SP6-RNA polymerase followed by translation in a wheat germ system in the presence of [35S] methionine. A typical reaction contained 8 $\mu$g plasmid DNA, 50 units SP6 polymerase (Epicentre Technologies, Madison, Wis.). 0.5× transcription salts (Promega), 80 $\mu$g/mL bovine serum albumin, 8 mM dithiotreitol, 40 $\mu$M each ATP, CTP, UTP and 8 $\mu$M GPT, 2 units RNasin (Boehringer Mannheim), 45 $\mu$M Cap (m7G(5')ppp(5')G, Boehringer Mannheim) in a volume of 22 $\mu$L for 30 min at 42° C. Additional GTP (40 $\mu$M) was added and the reaction incubated at 42° C. for a further 30 min. Typically 20 $\mu$L of the transcription reaction was translated in a wheat germ system (Amersham International) containing a 20.7 $\mu$L wheat germ extract, 83 mM potassium acetate, 50 $\mu$M each amino acid (minus methionine) and 60 $\mu$Ci (1000Ci/mmol) [35S] methionine in a volume of 110 $\mu$L at 25° C. for 30 min.

Protein Import Reaction

Intach pea chloroplasts were prepared as described by Madueño et al., 1992) and contained intact pea chloroplasts equivalent to 200 $\mu$g chlorophyll, 109 $\mu$L of the translation reaction, 1 mM methionine and 5 mM ATP in a final volume of 600 $\mu$L of import buffer (50 mM Hepes-KOH pH 8.0, 330 mM sorbitol). At the end of the incubation thermolysin was added to 100 $\mu$g/mL and incubated on ice for 30 min. Intact chloroplasts were reisolated (Madueño et al., 1992) and 5 $\mu$g chlorophyll was electrophoresed on an SDS-15% polyacylamide gel (Laemmli, 1970).

Chloroplast Fractionation Procedure

To isolate total envelope membranes the import reaction (see above, 200 $\mu$g chlorophyll/600 $\mu$L reaction) was treated with thermolysin (100 $\mu$g/mL) after which intact chloroplasts were reisolated, washed once in 0.8M sucrose in lysis buffer (10 mM Tricine-NaOH pH 7.6, 2 mM EDTA) and finally resuspended at 8 mg chlorophyll/mL in 0.8M sucrose in lysis buffer. Additional chloroplasts (100 $\mu$g chlorophyll) were added to the labelled chloroplasts and chloroplasts were lysed by diluting to 0.3 mg chlorophyll/mL with lysis buffer. Chloroplasts (1.15 mL) were fractionated by centrifugation (Beckman SW40 rotor, 75,000× g, 60 min. 4° C.) through the discontinuous sucrose step gradient described by Douce et al. (1973) except all sucrose solutions were in lysis buffer. Four fractions were collected. The stroma was in the top 1.15 mL of the gradient, the envelopes at the 0.6M/0.93M sucrose interface, mixed-thylakoids at the 0.93M/1.2M sucrose interface and the thylakoids at the 1.2M/1.5M sucrose interface. The membranes were diluted with lysis buffer, pelleted by centrifugation (100,000× g, Beckman SW40 rotor, 60 min, 4° C.) and resuspended in 0.3 M sucrose in lysis buffer.

When envelopes were treated with alkali the isolated total envelope membrane fraction was resuspended in 50 $\mu$L lysis buffer. Half the membranes were pelleted at 30 psi for 15 min in a Beckman Airfuge, resuspended in 0.1NaOH (100 $\mu$L), incubated on ice for 30 min, the membranes pelleted, washed once in lysis buffer and finally resuspended in lysis buffer (25 $\mu$L).

To separate inner and outer envelope membranes the import reaction contained 100 $\mu$g chlorophyll and the same constituents as above in a total volume of 600 $\mu$L. After thermolysin treatment (100 $\mu$g/mL, 30 min, 4° C.) intact chloroplasts were reisolated, washed once with import buffer and resuspended at 1 mg chlorophyll/mL in 0.6 M sucrose in lysis buffer. Chloroplasts were lysed by a freeze-thaw procedure (Keegstra and Yousif, 1986) and similarly lysed nonradiolabelled chloroplasts (400 $\mu$g chlorophyll) were added. Chloroplasts were diluted to 0.3M sucrose and 0.5 mg chlorophyll/mL with lysis buffer and 0.95 mL layered onto a discontinuous sucrose step gradient (Keegstra and Yousif, 1986). The gradient was centrifuged in a Beckman SW40 rotor at 75,000× g for 3 h at 4° C. and four fractions collected. The stroma was in the top 0.95 mL of the gradient, the outer envelopes at the 0.46M/0.8 M sucrose interface, the inner membranes at 0.8M/1.0M sucrose interface and the thylakoids at the 1.0M/1.5M sucrose interface. The membranes were diluted with lysis buffer, pelleted by centrifugation (100,000× g, Beckman SW40 rotor, 90 min, 4° C. and resuspended as above.

Protein was estimated by a modified Lowry procedure (Peterson, 1977) and 10 $\mu$g protein electrophoresed on SDS-15% polyacrylamide gels (Laemmli, 1970). Proteins were transferred (Towbin et al., 1979) to nitrocellulose (Schleicher and Schuell) and radiolabelled proteins were detected by exposure to Hyperfilm-Bmax (Amersham International). The same filters were probed with antibodies to the 30 kD spinach inner envelope membrane protein (E30; Joyard et al., 1982). Bound antibodies were detected using the ECL system according to the manufacturer's instructions (Amersham International). The amount of imported protein and endogenous PT (E30) were quantified by scanning autoradiographs with a Molecular Dynamics 300A laser scanning densitomer).

RESULTS

The Phosphate Translocator Presequence Contains Stromal Targeting Information

To determine whether the presequence of the phosphate translocator contains information for targeting the mature protein to the chloroplast envelope the chimaeric protein pPT-S (shown diagrammatically in FIG. 1A) was produced. This protein comprises the 73 amino acid residue presequence and the first 4 amino acid residues of the mature PT protein fused to the stromally located small subunit of ribulose-1, 5-bisphosphate carboxylase. A precursor protein (P) of approximately 25 kD was produced in a wheat germ translation system primed with the pPT-S transcript (FIG. 1A, track P). The precursor protein was imported by isolated pea chloroplasts and processed to a protein of approximately 15 kD (FIG. 1A, track I). These sizes are in close agreement with those calculated for the precursor (23 kD) and the mature protein 15 kD), if the PT cleavage site (P-C-P-A), retained during the production of this construct, was used. The efficiency of import of pPT-S relative to SSU Rubisco (pS-S) is shown in Table 1. Replacing the authentic SSU Rubisco presequence with that of the PT only marginally reduced the efficiency of the import of pS-S. Import of pPT-S was 83% of pS-S (Table 1).

Chloroplasts were lysed hypotonically and the stroma (S), a total envelope fraction (E), a mixed envelope-thylakoid fraction (ET) and a thylakoid membrane fraction (T) were isolated on a discontinuous sucrose gradient (FIG. 1A). As a control an identical fractionation was performed after import of the precursor of the SSU Rubisco (pS-S, FIG. 1B). The distribution of the imported pPT-S was identical to pS-S (FIG. 1C). The quantification of imported protein in FIG. 1C is plotted as density (amount of imported protein) in each fraction and as such gives an indication of enrichment in the particular fraction. Subsequent quantifications are also shown on this basis (FIGS. 2A–B, 3A–D and 4A–C). The majority of imported pPT-S and pS-S was in the stromal fraction but low levels were also present in the envelope and envelope-thylakoid fractions. This is probably due to the entrapment of stroma during chloroplast lysis and membrane vesiculation. Washing of membranes did not remove this contamination (see FIGS. 1A–C legend). These data suggest that the PT presequence contains stromal-targeting information and that the mature phosphate translocator is responsible for envelope-membrane targeting.

Envelope-targeting Information Resides in the Mature Phosphate Translocator Protein If the mature PT protein contains envelope targeting information, replacing the PT presequence with that of the SSU Rubisco should make no difference to the localisation of the imported protein. To test this hypothesis the chimaeric protein pS-PT (shown diagrammatically in FIG. 2A) was produced. This protein comprises the 57 amino acid residue SSU Rubisco presequence fused to amino acid residues 3 to 330 of the mature PT protein. Translation of the pS-PT transcript produced a 36 kD precursor protein (FIG. 2A(i), track P) which was processed to a protein of approximately 32 kD after import by pea chloroplasts (FIG. 2A(i), track I). These protein migrate faster than expected; however the normal mature pea PT protein also migrates anomalously (32 kD; FIG. 2B(i), track I) compared to the expected size of 36 kD (Willey et al., 1991), in this gel system.

To determine the location of the imported chimaeric protein, chloroplasts were fractionated and the stroma (S), envelopes (E), mixed envelopes-thylakoids (ET) and thylakoid membranes (T) were isolated (FIG. 2A(ii)). As a control an identical fractionation procedure was performed on chloroplasts after import of the PT precursor protein (pPT-PT), FIG. 2B(ii)). Protein was found in E and ET fractions with a little in T and non in S. The distribution of pS-PT was identical to that of imported pPT-PT and the endogenous PT protein (FIG. 2A) which strongly suggests that the mature PT protein contains envelope-targeting information. Replacing the PT presequence with that of the SSU Rubisco had a significant effect on the efficiency of the import of the chimaeric precursor protein. The import of pS-PT was 25% of the authentic phosphate translocator protein (Table 1). This suggests that the presequence, although not appearing to affect targeting (see FIGS. 2A–B), does affect the efficiency of the import process.

Endogenous PT protein was assessed by the electrophoresis of fractions on SDS-PAGE, blotting to nitrocellulose and the same filter being subjected to autoradiography to detect imported protein and probed with antibodies raised against the spinach PT protein (E30; Joyard et al., 1982). The imported PT comigrated with the upper band (32 kD) of the doublet of endogenous PT protein in FIG. 2B(iii). A quantification of this and imported protein is shown in FIG. 2B(iv). The assessment of endogenous PT protein was deemed necessary as a large proportion (approximately 85%) of the imported PT protein was found in the thylakoid membrane fraction. This is not due to mistargeting of the PT protein during import but to contamination of the thylakoid fraction with envelope membranes. A similar level of contamination has been found by other workers (Murakami and Strotmann, 1978; Andrews et al., 1985, Li et al., 1992) and was confirmed by an assessment of the distribution of the envelope membrane marker galactosyl transferase (Douce and Joyard, 1979) which showed an identical distribution to that of the endogenous and the imported PT proteins (data not shown). Endogenous PT protein, determined by probing with E30 antibodies, was subsequently used as an internal control in chimaeric construct import experiments.

Figure 3A:
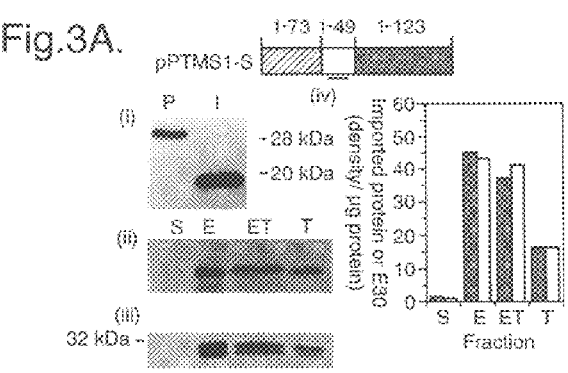
Figure 3B:
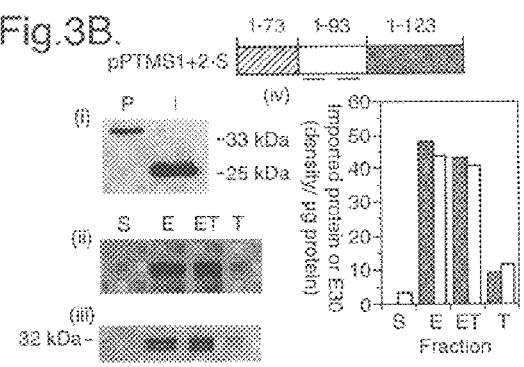
Figure 3C:
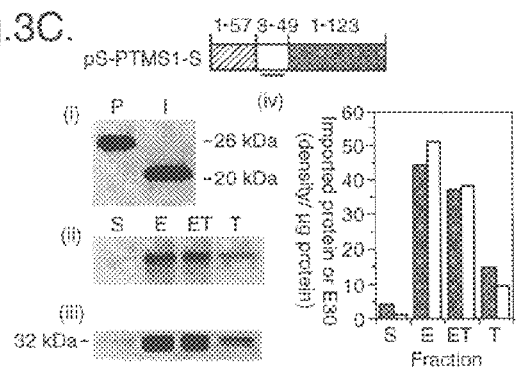
Figure 3D:
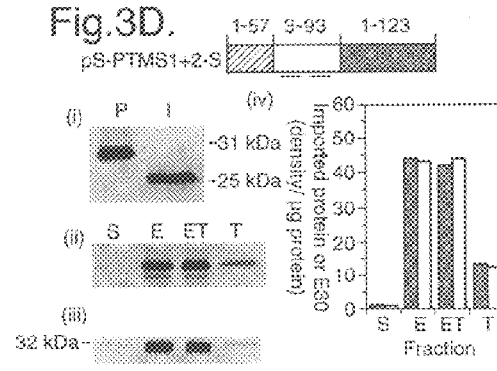
Figure 5A:
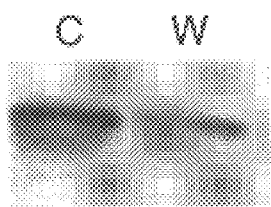
Figure 5B:
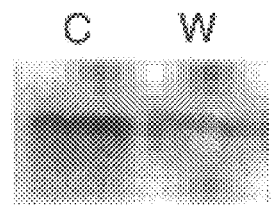
Figure 5C:
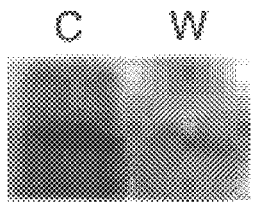
Figure 5D:
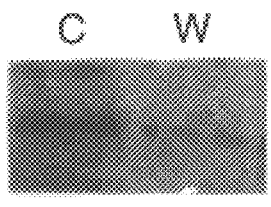
Figure 5E:
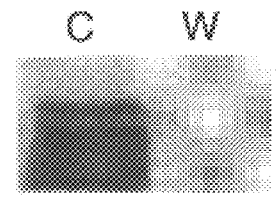
Figure 5F:
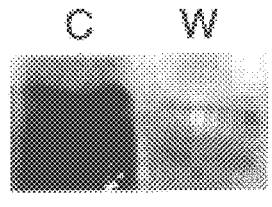

The N-terminal Region of the Mature Phosphate Translocator Protein Contains Envelope Targeting Information To define which region of the mature PT protein contains envelope-targeting information four chimaeric proteins containing the N-terminal region of the PT were produced. The first two proteins contained the PT presequence and either the first or the first and second N-terminal putative membrane-spanning regions of the mature PT protein fused to the SSU Rubisco mature protein. The chimaeric protein pPTMS1-S contains the presequence and residues 1 to 49 of the mature PT (FIG. 3A), whereas pPTMS1+2-S contains the presequence and residues 1 to 93 of the mature PT protein (FIG. 3B). In the second set of constructs either the first or first and second N-terminal membrane spans of the mature PT protein were placed between the SSU Rubisco presequence and mature protein to produce pS-PTMS1-S (amino acid residues 3–49, FIG. 3C) or pS-PTMS1+2-S (amino acid residues 393, FIG. 3D). Translation of the transcripts in a wheat germ system produced precursor proteins of 28 kD for pPTMS1-S, 33 kD for pPTMS1+2-S, 26 kD for pS-PTMS1-S and 31 kD for pS-PTMS1+2-S (FIGS. 3A(i)–D(i), track P). These are all close to their expected sizes; 20 kD for pPTMS1-S and pS-PTMS1-S (FIGS. 3A(i) and 3C(i), track I) 25 kD for pPTMS1+2-S and pS-PTMS1+2-S (FIGS. 3B(i) and 3D(i), Track I). Again the efficiency of import of these chimaeric proteins appeared to be reduced when the authentic PT presequence was replaced with that of the SSU Rubisco. The import of pPTMS1-S and pPTMS1+2-S were equivalent to pPT-PT whereas import of pS-PTMS1-S and pS-PTMS1+2-S were 38% of the PT level (Table 1).

Sub-chloroplast fractions were isolated after import of these chimaeric proteins to determine if envelope targeting had occurred. The distribution of imported protein (FIGS. 3A(ii)–3D(ii)) and endogenous PT protein (FIGS. 3A(iii)–3D(iii)) within the chloroplast sub-fractions indicated that all four imported proteins were associated with the chloroplast envelope membrane (FIGS. 3A(iv)–3D(iv)). These results confirm our previous finding that the PT presequence is not required for envelope-targeting and more importantly show that the N-terminal region of the mature phosphate translocator protein (amino acid residues 3–49) can direct a normally stromally-targeted protein to the chloroplast envelope.

Envelope-targeting Information Resides in the N-terminal Hydrophobic Region of the Mature Phosphate Translocator Protein The N-terminal region of the mature phosphate translocator protein, capable of causing association of the SSU Rubisco with the chloroplast envelope membrane, comprises a potential α-helical membrane-spanning region (amino acid residues 24–45) flanked by hydrophilic regions. The hydrophilic region N-terminal to the α-helix contains 3 negatively charged Asp7, Glu11, Glu12) and 2 positively charged (Lys13, Arg22) amino acid residues whereas 2 positively charged residues (Lys47, Lys48) are located C-terminal to the putative membrane span. To define further the regions involved in targeting to the envelope membrane chimaeric proteins containing different regions from the PT protein located between the presequence and mature regions of the SSU were produced. The precursor of the chimaeric protein, pS-+MS-S, containing amino acid residues of 7 to 45 of the mature PT which includes the putative membrane span and the 16 hydrophilic amino acid residues N-terminal to it, had a molecular mass of 27 kD (FIG. 4A(i), track P). This precursor was imported by isolated pea chloroplasts and processed to a major 20 kD and a minor 14 kD product (FIG. 4A(i), track I). The precursor and the major processed product were close to their predicted sizes of 25 kD and 19 kD respectively. The import of this chimaeric protein was 13% of the authentic PT protein (Table 1). After import the 20 kD protein was associated with the envelope fraction having a distribution close to that of the endogenous PT protein assessed by Western blotting (FIGS. 4A(ii)–(iv)). This suggests that the hydrophilic region C-terminal to the hydrophobic membrane-spanning region was not required for targeting to the inner envelope membrane but may effect the efficiency of this process.

The precursor chimaeric protein, pS-MS+-S, containing amino acid residues 24 to 49 which includes the putative membrane-spanning region and the 4 amino acid residues C-terminal to it, had a molecular mass of approximately 25 kD (FIG. 4B(i), track P). This is close to the predicted size of 24 kD. The precursor was imported, although rather inefficiency (16% of pPT-PT level; Table 1), by isolated pea chloroplasts (FIG. 4B(i), track I) to produce a number of products ranging in size from the precursor (25 kD) to approximately 19 kD. The latter is close to the predicted size of the mature protein. When chloroplasts were fractionated after import of pS-MS+-S, the precursor (25 kD) and proteins of approximately 21 kD and 20 kD were associated with the envelope membranes (FIGS. 4B(ii) & (iii)) whereas a group of proteins of approximately 23 kD and a 19 kD protein were found in the stromal fraction. These proteins can be seen more clearly with a higher loading of the stromal fraction (FIG. 4B(ii), track Sx3). These data suggest that after import of this chimaeric protein the subset of processed products associated with the envelope membrane is distinctly different from those found in the stromal fraction. This subset was subsequently shown not to be integrated into the envelope membrane (see FIGS. 5A–F).

The precursor of the chimaeric protein, pS-MS-S, containing solely the putative hydrophobic membrane-spanning region (amino acid residues 24–45) without the flanking hydrophilic residues, had a molecular mass of 23 kD, identical to its predicted size (FIG. 4C(i), track P). This chimaeric protein, like pS-MS+-S, was inefficiently imported by pea chloroplasts (9% of pPT-PT level; Table 1) and resulted in the production of a number of protease-resistant products ranging in size from the unprocessed precursor (23 kD) to approximately 18 kD. After fractionation all these products were associated with the envelope membrane (FIGS. 4C(ii) & (iii)). This suggests that the N-terminal membrane span of the mature phosphate translocator protein is the only requirement for envelope targeting.

The multiple processed products observed after the import of the chimaeric proteins pS-MS+-S and pS-MS-S suggest that some non-specific processing has occurred within the SSU presequence. This has often been observed after import of fusion proteins into chloroplasts (Li et al., 1992) and the import of a SSU Rubisco mutant with an alteration at the C-terminus of the presequence was shown to produce a number of products of similar sizes to those observed in this study (Ostrem et al., 1989). Because of these products quantitation of the fractionation after import of pS-MS+-S and pS-MS-S (FIGS. 4B & C) was not attempted.

Imported Chimaeric Proteins are Integrated into the Envelope Membrane

To test whether imported chimaeric proteins were integrated into the envelope, or merely associated with the envelope membrane because of their hydrophobic nature, isolated envelope membranes were washed with 0.1M NaOH. Resistance to NaOH-treatment is an indication that the polypeptide has penetrated the membrane's hydrophobic core (Steck and Yu, 1973). Results of such treatments are shown in FIGS. 5A–F and the resistance to NaOH-treatment in comparison to the authentic PT protein is quantified in Table 2. The chimaeric proteins pS-PT and pS-PTMS1-S were integrated into the envelope membrane to the same extent as the authentic PT protein. The percentage of authentic imported PT recovered in NaOH-treated envelope membranes was 35% of the unwashed control (see Table 2). The reason for this reduction is unknown but may be due to inefficiency of pelleting of envelope membranes after the NaOH-treatment. Other workers have obtained very similar results after extraction of envelope membranes with 0.1M NaOH (Waegemann and Soll, 1991). The envelope-associated products of the import of pS-+MS-S and pS-MS-S were also integrated into the envelope membrane although to a lesser extent than that of the authentic PT protein whereas envelope-associated products of pS-MS+-S import were washed off the membrane by the NaOH treatment.

The N-terminal Hydrophobic Region of the Mature Phosphate Translocator Protein Directs the SSU Rubisco to the Chloroplast Inner Envelope The previous experiments suggest that the N-terminal hydrophobic region of the mature phosphate translocator protein can target the SSU Rubisco to the chloroplast envelope. To determine whether targeting was to the inner envelope membrane, the sub-envelope location of five of the imported chimaeric proteins was determined (FIGS. 6A–F). Chloroplasts were hypertonically lysed to enable separation of inner and outer envelope membranes.

The PT precursor protein (pPT-PT) was imported by pea chloroplasts and sub-chloroplast fractions including the stroma (S), outer envelope (OE), inner envelope (IE), and thylakoid (T) membranes were isolated. The distribution of both the imported and endogenous PT proteins in these fractions were very similar (FIG. 6A) but suggested that there was a low level of inner envelope contamination of the outer envelope fraction. Contamination has also been found by other workers (Block et al., 1983; Li et al., 1992). The same distribution is seen for imported pS-PT (FIG. 6B) confirming previous results (FIGS. 2A–B) that strongly suggested that PT targeting information is located in the mature protein. Comparison of the imported pS-PTMS1-S and the endogenous PT protein (FIG. 6C) shows that, although targeting was to the inner envelope membrane, a considerable portion of the imported protein was found in the stromal fraction. This form was barely visible in the stromal fraction in previous, total envelope fractionation experiments (FIGS. 3A). The reason for this difference is unknown.

Figure 6A:
Figure 6D:
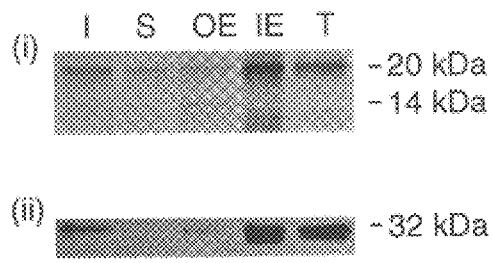
Figure 6B:
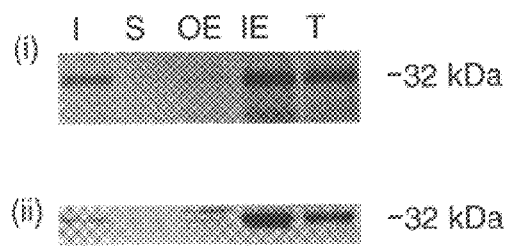
Figure 6E:
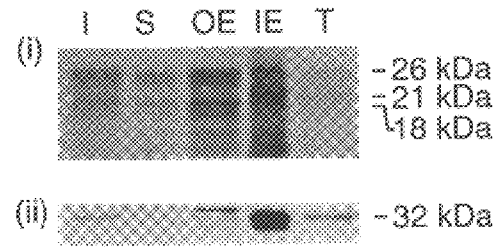
Figure 6C:
Figure 6F:
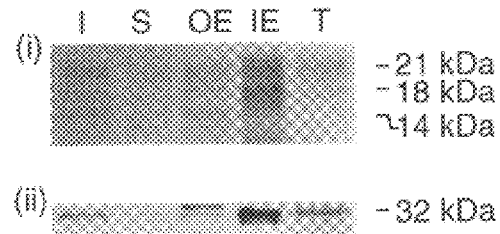

The major product after pS-+MS-S import (20 kD) was associated with the inner envelope membrane (FIG. 6D). Separation of inner and outer envelope membranes after pS-MS+-S import showed association of the precursor protein (26 kD) and a processing intermediate of approximately 21 kD with the inner envelope membrane. The remaining processing intermediates and a protein of approximately 18 kD, close in size to the mature MS+-S protein, were stromally located (FIG. 6E). A NaOH-treatment of the total envelope fraction suggests that these envelope-associated proteins were not integrated into the membrane (see FIGS. 5A–F). When the surrounding charged amino acid residues were removed (pS-MS-S; FIG. 6F), the mature protein (MS-S, predicted to be 18 kD) was associated with the inner envelope membrane. This suggests that the only requirement for targeting the normally stromally-located SSU Rubisco to the inner envelope membrane is the N-terminal hydrophobic region of the mature phosphate translocator protein.

DISCUSSION

The results provided herein have clearly demonstrated that the presequence of the phosphate translocator is not responsible for envelope targeting. Analysis of the presequences of the PT and a 37 kD inner envelope membrane protein suggested the presence of features distinguishing these from other stromal or thylakoid targeted proteins and so it was suggested that the presequence could be responsible for envelope targeting (Willey et al., 1991, Dreses-Werringloer et al., 1991). This is clearly not the case of the phosphate translocator resequence and has similarly been demonstrated for the maize amyloplast envelope Bt1-encoded protein (Li et al., 1992). Replacement of the PT resequence does however reduce the efficiency of import suggesting co-evolution of the PT presequence to suit this very hydrophobic passenger protein. Subunit 8 of *Neurospora crassa* F1Fo ATPase, another very hydrophobic protein, could be targeted to the mitochondria only using the presequence of the equally hydrophobic subunit 9 of the ATPase (Gearing and Nagley, 1986). The data here indicate that the PT presequence functions as a chloroplast-import and not an envelope-targeting signal. The information for targeting the PT to the inner envelope membrane must therefore reside within the mature protein.

The N-terminal hydrophobic region of the mature phosphate translocator can target and cause integration of the SSU Rubisco into the inner envelope membrane.

Targeting of Proteins to Inner Plastid Envelope in Transgenic Plants

Preparation of Constructs

Two chimaeric gene constructs were prepared, pMS1-uhpT and pMS1+2-uhpT, and placed under the control of two different promoters.

Both constructs were prepared from the plasmids pPTMS1-S and pPT MS1+2-S and pBST. pPTMS1-S and pPT MS1+2-S have been constructed in the vector pSP65 (Promega) and consist of the pea phosphate translocator transit peptide (Willey et al., 1991) and either the first or first and second putative membrane spans of the mature phosphate translocator attached (in frame) to hepea SSU Rubisco (Anderson et al., 1986). pBST was constructed in the vector, pBluescript KS+ (Stratagene), and contains a fragment of uhpT (Friedrich and Kadner, (1987)), the *E. coli* sugar phosphate translocator.

pMS1-uhpT and pMS1+2-uhpT were prepared by digesting pPTMS1-S and pPTMS1+2-S with EcoRI and BamHI and cloning the insert into EcoRI BamHI digested pBCSK+ (Stratagene). This plasmid was then digested with SphI and BamHI to remove the sequence encoding the SSU Rubisco and a SphI BamHI fragment of uhpT was cloned in its place. This SphI BamHI fragment of uhpT was prepared by using PCR to introduce in frame SphI, EcoRI and BamHI restriction sites. The sense primer was 5'-CGC GCG CAT GCT GGC TTT CTT AAA CCA GG-3' (SEQ ID NO:11) where the underlined portion represents the SphI site, and the antisense primer was 5'-CGG GAT CCG AAT TCT TAT GCC ACT GTC AAC TGC TH-3' (SEQ ID NO:12), where the underlined portion represents the BamHI and EcoRI sites respectively.

The chimaeric gene construct was digested with EcoRI and cloned into the EcoRI site of the palindromic plasmid pRL424. The inserts were subsequently digested with BamHI and cloned into ether BamHI digested pROK2 (pBIN19 (Bevan, M. W. NAR above) containing the CAMV 35S promoter and nos terminator) or pFW4101 (containing the patatin promoter) after the removal of GUS. pFW4101 was deposited at the National Collection of Industrial and Marine Bacteria, Aberdeen, GB on Jul. 5, 1990 under accession number NCIMB 40306.

Preparation of Chloroplast Envelope Membranes

Chloroplast envelope membranes were prepared by grinding 0.2 g of leaf disc in 1 mL ice cold 10 mM Tricine-NaOH pH 7.5, 2 mM EDTA in an ice cold mortar. Cell wall debris and starch was removed by centrifugation at 2000× g for 30 g at 4° C. The supernatant was layered onto a discontinuous sucrose density gradient consisting of 9 mL 0.6M sucrose, 10 mM Tricine and 4 mL 1.0M sucrose, contained in a 14 mm×95 mm Beckman ULTRA-CLEAR™ ultracentrifuge tube and was subjected to ultracentrifugation at 113,600× g for 2 hr at 4° C. The envelope membrane enriched interface between the 0.6M and 1.0M sucrose was transferred to a clean ULTRA-CLEAR™ tube, washed with 14 mL 10 mM Tricine-NaOH pH 7.5, 2 mM EDTA. Membranes were isolated by ultracentrifugation at 192,000× g for 1 hr at 4° C. The membrane pellet was resuspended at 50 $\mu$L 10 mM Tricine-NaOH pH 7.5, 2 mM EDTA and stored at −20° C. until use. Envelope proteins were subjected to SDS-PAGE in 10 $\mu$L aliquot of membrane resuspension.

SDS-PAGE and Western Analysis

Aliquots of membrane resuspension were subjected to SDS-PAGE using a 12% polyacrylimide resolving gel run at 80 V for 2 hrs. The gels were soaked in transfer buffer (14.4% glycine, 0.3% Tris, 0.1% SDS, 20% methanol) for 30 min prior to transfer and the proteins were transferred to nitrocellulose using a semi dry blotting system, 8 V for 1 hr. The membrane was blocked overnight at 4° C. in either 3% bovine serum albumin (BSA) or 5% non-fat dried milk powder (Marvel) dissolved in phosphate buffered saline (PBS=0.8% NaCl, 0.02% KCl, 0.144% $Na_2HPO_4$, 0.024% $KH_2PO_4$ (all w/v)) containing 0.1% Tween-20. The membrane was rinsed with 0.1% Tween-20 in PBS for 5 min and then probed with primary antibody (1:5000) in 1% BSA, 0.1% Tween-20 in PBS for approximately 3 hrs at room temperature. The primary antibody was washed off by 3 washes (1×15 min, 2×5 min) in 0.1% Tween-20 in PBS and secondary antibody conjugated to biotin was added to the membranes (1:1000) in 1% BSA, 0.1% Tween-20 in BPS, and incubated at room temperature for approximately 1 hr.

The secondary antibody was washed away by 3 washes 0.1% Tween-20 in PBS (1×15 min, 2×5 min) and the membrane was incubated with streptavidin horse radish peroxidase, 1% BSA, 0.1% Tween-20 in PBS (1:5000) for a further hours. The membrane was washed 3 times in 0.1% Tween-20 in PBS (1×15 min, 2×5 min) and once in PBS (5 min). Antibody was detected using the ECL system (Amersham International), 4 ml of ECL reagents 1 and 2 were applied to the surface of the membrane for 1 min. The membrane was then drained, covered in cling film, and exposed to Hyperfilm-ECL.

Production of Transgenic Plants

Tobacco: Chimaeric gene constructs in binary vectors were transferred into *Agrobacterium tumefaciens* strain LBA4404 (Ooms et al., 1981) by electroporation (Shen and Forde, 1989) and the resulting strains were used to infect leaf discs of tobacco (*Nicotiana tabacum* cv. Samsum) essentially according to Horsch et al., (1989). The regenerated plants were dissected from callusing leaves and maintained in sterile culture on MS media containing 200 μg/ml carbenicillin and 100 μg/ml kanamycin and subcultured every 2 weeks. The rooted transgenic plants obtained within 10–12 weeks were transferred to soil and acclimatised in a propagator before growth in a controlled environment room (Fisons Sanyo). The plants were allowed to flower, inflorescences were bagged to ensure self-pollination and resulting seed was collected as the $T_1$ generation. Analysis of the leaves from these plants showed that the sugar phosphate translocator was transported to the inner envelope.

Potato: *Agrobacterium tumefaciens*-mediated transformation methods were used to infect leaf discs of potato (*Solanum tuberosum* cv. Prairie) essentially according to Horsch et al. (1989). Infected discs were allowed to grow on MS medium containing 3% sucrose for 3 days and transformants were selected on media described by Blundy et al., (1991). Callus was induced on MS medium supplemented with 2.5 mg/l benzylaminopurine, 0.1 mg/l naphthalene acetic acid, 10 mg/l gibberellic acid ($GA_3$), 500 mg/l claforan and 50 mg/ml kanamycin. Calli were transferred to MS medium containing 2.5 mg/l benzylaminopurine and 10 mg/l $GA_3$ for shoot induction. Shoots were excised and cultured on liquid MS medium without hormones and subcultured every 2 weeks. Strong shoots were transferred onto solid MS medium without hormones to make then sturdy. Microtubers were inducted by placing the nodal cuttings from the sturdy shoots in MS medium supplemented with 6% sucrose, 2.5 mg/l kinetin and 180 mg/ml ancymidol. Tubers were induced after 5–6 weeks incubation in dark at 19° C.

REFERENCES

Anderson, S. and Smith, S. M. (1986). Biochem. J. 240, 709–715.

Andrews, et al. (1985). Plant Physiol. 78, 459–465

Auchinocloss, et al. (1992). J. Biol. Chem. 267, 10439–10446.

Barnes, et al. (1994) Plant Physiol. 106, 1123–1129.

Beasley, et al. (1993). EMBO J. 12, 2303–2311.

Beltzer, et al. (1991). J. Biol. Chem. 266, 973–978.

Block, et al. (1983). J. Biol. Chem. 25, 13281–13286.

Blundy, et al., (1991). Plant Mol. Biol. 16, 153–160.

Cheung, et al. (1988). Proc. Natl. Acad. Sci. USA 85, 391–395.

Cline, et al. (1985). J. Biol. Chem. 260, 3691–3969.

Cline, et al. (1989). J. Biol. Chem. 264, 14225–14232.

de Boer, et al. (1991). Biochim. Biophy. Acta. 1071, 221–253.

Douce, et al. (1979). Adv. Bot. Res. 7, 1–116.

Douce, et al. (1973), J. Biol. Chem. 248, 7215–7222.

Dreses-Werringloer, et al. (1991). Eur. J. Biochem. 195, 361–368.

Fischer, et al. (1994) Plant Mol. Biol. 25, 167–177.

Fliege, et al. (1978). Biochim. Biophys, Acta. 502, 232–247.

Flügge, et al. (1979) In: Quagliariello, E., Palmieri, F., Papa, S. and Klingenberg, E. M. (eds.) Functional and molecular aspects of biomembrane transport. Elsevier-North Holland, Amsterdam, pp. 373–382.

Flügge, et al. (1989). EMBO J. 8, 39–46.

Friedrich, M. J. and Kadner, R. J. (1987). J. Bacteriology 169, 3556–3563.

Gavel, et al. (1992). Eur. J. Biochem. 205, 1207–1215.

Gavel, et al. (1991). FEBS Lett. 282, 41–46.

Gearing, et al. (1986). EMBO J. 5, 3651–3655.

Glick, et al. (1992). Sci. 17, 453–459.

Hirsch, et al. (1994). Science 266, 1989–1992.

Horsch, et al., (1985). Science 227, 1229–1231.

Jensen, et al. (1992). Mol. Cell Biol. 12, 4677–4686.

Joyard, et al. (1982). J. Biol. Chem. 257, 1095–1101.

Keegstra, et al. (1986). Meth. Enzymol. 118, 316–325.

Keegstra, et al. (1989). Ann. Rev. Plant Physiol. Plant Mol. Biol. 40, 471–501.

Knight, et al. (1994). Mol. Gen. Genet. 242, 586–594.

Ko, et al. (1992). J. Biol. Chem. 267, 2986–2993.

Kohorn, et al. (1989). Plant Cell 1, 159–166.

Koll, et al. (1992). Cell 68, 1163–1175.

Kuroiwa, et al. (1990). J. Biochem. 108, 829–834.

Laemmli, U. K. (1970). Nature 227, 680–685.

Li, et al. (1992). Science 256, 1815–1817.

Li, et al. (1991). Plant Cell 3, 709–717.

Li, et al. (1992). J. Biol. Chem. 267, 18999–19004.

Lubben, et al. (1987). Science 238, 1112–1113.

Madueño, et al. (1994). J. Biol. Chem. 269, 17458–17463.

Madueño, et al. (1992). Plant Mol. Biol. 20, 289–299.

Madueño, et al. (1993). Plant cell 5, 1865–1876.

Murakami, et al. (1978). Arch. Biochem. Biophys. 185, 30–38.

Oblong, et al. (1978). EMBO J. 11, 4401–4409.

Ooms, et al., (1981). Gene 14, 33–50

Ostrem, et al. (1989). J. Cell Biol. 264, 3662–3665.

Payan, et al. (1991). J. Cell Biol. 112, 603–613.

Perry, et al. (1994). Plant Cell 6, 93–105.

Peterson, G. (1977). Anal. Biochem. 83, 346–356.

Pfanner, et al. (1987). J. Biol. Chem. 262, 14851–14854.

Salomon, et al. (1990). Proc. Natl. Acad. Sci., USA 87, 5778–5782.

Schnell, et al. (1994) Science 266, 1007–1012.

Schulz, et al. (1993). Mol. Gen. Genet. 238, 357–361.

Steck, et al. (1973) J. Supramol. Struct. 1, 220–232.

Sullivan, et al. (1991). Plant Cell 3, 1337–1348.

Swift, et al. (1991). J. Cell Biol. 115, 19–30.

Towbin, et al. (1979(. Proc. Natl. Acad. Sci. USA 76, 4350–4354.

von Heijne, G. (1986). EMBO J. 5, 3021–3027.

von Heijne, et al. (1988). Eur. J. Biochem. 174, 671–678.

Waegemann, et al. (1991) Plant J. 1, 149–158.
Willey, et al. (1991). Planta 183, 451–461.
Wu, et al. (1994) J. Biol. Chem. 269, 32264–32271.
Zabaleta, et al. (1994) Plant J. 6, 425–432.

SEQ ID NO: 1
PALTTGFFFFTWYFLNVIFNIL

SEQ ID NO: 2
5'-CCAGCTCTTACTACCGGTTTTTTCTTCTTCACTT
GGTACTTCTTGAATCTCATTTT CAACATCCTC

TABLE 1

Efficiency of import of Chimaeric Proteins by Pea Chloroplasts

| Control Protein | Protein | Import Efficiency[a] |
|---|---|---|
| pS-S[b] | pS-S | 100 |
|  | pPT-S | 83 |
| pPT-PT[c] | pPT-PT | 100 |
|  | pS-PT | 25 |
|  | pPTMS1-S | 100 |
|  | pPTMS1 + 2-S | 100 |
|  | pS-PTMS1-S | 38 |
|  | pS-PTMS1 + 2-S | 38 |
|  | pS- + MS-S[d] | 13 |
|  | pS-MS + S[d] | 16 |
|  | pS-MS-S[d] | 9 |

[a]The % imported precursor protein in a protease-resistant location after import by pea chloroplasts, over 30 min, was assessed by quantitation of autoradiographs by laser scanning densitometry. Efficiency is shown relative to control protein import.

TABLE 1-continued

Efficiency of import of Chimaeric Proteins by Pea Chloroplasts

| Control Protein | Protein | Import Efficiency[a] |
|---|---|---|

[b],[c]The efficiency of pS-S import was 18% and pPT-PT was 8% of input precursor protein.
[d]All imported products were included in the quantitation.

TABLE 2

Extractability of Envelope-associated Chimaeric Proteins with 0.1 M Sodium Hydroxide.

| Protein | Protein in Washed Envelopes (% pPT-PT level) |
|---|---|
| pPT-PT | 100 |
| pS-PT | 97 |
| pS-PTMS1-S | 103 |
| pS- + MS-S | 57 |
| pS-MS + -S | 0 |
| pS-MS-S | 34 |

Imported protein was quantified by scanning as described in FIGS. 1A–C. The association of imported chimaeric protein with NaOH-treated enveloped is expressed as a % of the control (pPT-PT) associated level.

What is claimed is:

1. A method of targeting a protein or polypeptide to the inner envelope membrane of a plastid of a plant cell, comprising
    introducing a chimaeric gene comprising a promoter, a coding sequence for a chimaeric protein, and a terminator sequence, into a plant cell;
    wherein the promoter is capable of expressing the chimaeric protein in the plant cell; and
    wherein the coding sequence comprises a first nucleotide sequence encoding a first polypeptide consisting essentially of an amino terminal hydrophobic region of a mature phosphate translocator protein, said mature phosphate translocator protein residing in the inner envelope membrane of a plastid; and a second nucleotide sequence encoding a second heterologous protein or polypeptide which is to be targeted to the inner envelope membrane of a plastid.

2. The method according to claim 1 wherein the promoter is a CaMV 35 S promoter or a patatin promoter.

3. The method according to claim 1 wherein the amino terminal hydrophobic region of a mature translocator protein has the amino acid sequence set forth in SEQ ID NO: 1.

4. The method according to claim 1 wherein the first nucleotide sequence consists essentially of the nucleotide sequence set forth in SEQ ID NO: 2.

5. The method according to claim 1 wherein the first nucleotide sequence encodes an amino acid sequence corresponding to the amino acid residues 1–49, 3–49, 1–93, 3–93, 7–45, or 24–49 of the mature pea phosphate translocator protein of which the amino acid sequence of amino acid residues 24–45 is set forth in SEQ ID NO: 1.

6. The method according to claim 1 wherein the first polypeptide consists essentially of a presequence of a translocator protein and an amino terminal hydrophobic region of a mature translocator protein.

7. The method according to claim 1 wherein the phosphate translocator protein is from pea, tobacco, spinach, or potato.

8. The method according to claim 1 wherein the second nucleotide sequence encodes a protein that is located in the stroma of a plastid.

9. The method according to claim 1 wherein the second nucleotide sequence encodes a reporter or a polypeptide that confers an identifiable character to a genetically engineered plant.

10. The method according to claim 1 wherein the second nucleotide sequence encodes an amino acid sequence or a functional portion thereof of a membrane transporter, a translocator protein, an enzyme, a protein or polypeptide involved in DNA replication, a protein or polypeptide involved in signal transduction, a protein or polypeptide involved in the control of the growth of cells, or a protein or polypeptide involved in the development of a plant.

11. The method according to claim 10 wherein the amino acid sequence is from an animal, plant, fungus or bacterium.

12. The method according to claim 10 wherein the membrane transporter is a glucose 6-phosphate transporter.

13. The method according to claim 10 wherein the membrane transporter transports sugars, amino acids, or metal ions.

14. The method according to claim 1 wherein the second nucleotide sequence encodes a hexose phosphate translocator or ADP glucose translocator.

15. The method according to claim 1 wherein the second nucleotide sequence encodes a translocator for an intermediate for a process selected from the group consisting of: starch synthesis, pigment synthesis, oil biosynthesis, and lipid biosynthesis.

16. The method according to claim 1 wherein the terminator sequence is nos.

17. The method according to claim 1 wherein the chimaeric gene is integrated into the genome of the plant.

18. The method according to claim 1 wherein the chimaeric gene is introduced into the plant by techniques selected from the group consisting of:
    Agrobacterium tumafaciens-mediated transformation, particle or microprojectile bombardment, electroporation, and direct DNA uptake.

19. The method according to claim 1 wherein the plastid is a chloroplast, an amyloplast, a leucoplast, or a chromoplast.

20. The method according to claim 1 wherein the method further comprises regenerating a plant from the plant cells to which the chimaeric gene was introduced.

21. The method according to claim 20 wherein the regenerated plant is a dicotyledonous species.

22. The method according to claim 20 wherein the regenerated plant is a monocotyledonous species.

23. The method according to claim 21 wherein the regenerated plant is selected from the group consisting of potato, tobacco, cotton, lettuce, melon, squash, cucumber, pea, rape, soybean, sugar beet, and sunflower.

24. The method according to claim 22 wherein the regenerated plant is selected from the group consisting of wheat, barley, rye, rice, and maize.

* * * * *